(12) United States Patent
Wang et al.

(10) Patent No.: US 8,121,249 B2
(45) Date of Patent: Feb. 21, 2012

(54) MULTI-PARAMETER X-RAY COMPUTED TOMOGRAPHY

(75) Inventors: Ge Wang, Blacksburg, VA (US); Wenxiang Cong, Christiansburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 12/794,160

(22) Filed: Jun. 4, 2010

(65) Prior Publication Data

US 2010/0310037 A1 Dec. 9, 2010

Related U.S. Application Data

(60) Provisional application No. 61/184,029, filed on Jun. 4, 2009.

(51) Int. Cl.
*A61B 6/00* (2006.01)
(52) U.S. Cl. ............... 378/6; 378/7; 378/70; 378/86
(58) Field of Classification Search ........... 378/6, 7, 378/86, 87
See application file for complete search history.

(56) References Cited

U.S. PATENT DOCUMENTS

| | | | |
|---|---|---|---|
| 4,651,002 A * | 3/1987 | Anno | 250/336.1 |
| 4,656,650 A * | 4/1987 | Kikuchi et al. | 378/7 |
| 5,313,511 A * | 5/1994 | Annis et al. | 378/87 |
| 5,987,095 A * | 11/1999 | Chapman et al. | 378/70 |
| 6,175,609 B1 * | 1/2001 | Edic et al. | 378/7 |
| 6,850,585 B2 | 2/2005 | Hsieh | |
| 7,145,980 B2 * | 12/2006 | Sakaguchi et al. | 378/7 |

(Continued)

OTHER PUBLICATIONS

Strobl et al., Small angle scattering signals for (neutron) computerized tomography, Applied Physics Letters, vol. 85, No. 3, Jul. 2004, pp. 488-490.*

(Continued)

*Primary Examiner* — Alexander H Taningco
(74) *Attorney, Agent, or Firm* — New River Valley IP Law; Michele L. Mayberry

(57) ABSTRACT

The present invention relates to the field of x-ray imaging. More particularly, embodiments of the invention relate to methods, systems, and apparatus for imaging, which can be used in a wide range of applications, including medical imaging, security screening, and industrial non-destructive testing to name a few. Specifically provided as embodiments of the invention are systems for x-ray imaging comprising: a) a first collimator-and-detector assembly having a first operable configuration to provide at least one first dataset comprising primary x-ray signals as a majority component of its data capable of being presented as a first image of an object subjected to x-ray imaging; b) a second collimator-and-detector assembly having a second operable configuration or wherein the first collimator-and-detector assembly is adjustable to a second configuration to provide at least one second dataset comprising primary and dark-field x-ray signals as a majority component of its data capable of being presented as a second image of the object; and c) a computer operably coupled with the collimator-and-detector assemblies comprising a computer readable medium embedded with processing means for combining the first dataset and the second dataset to extract the dark-field x-ray signals and produce a target image having higher contrast quality than the images based on the first or second dataset alone. Such systems can be configured to comprise at least two collimator-and-detector assemblies or configurations differing with respect to collimator height, collimator aperture, imaging geometry, or distance between an object subjected to the imaging and the collimator-and-detector assembly.

22 Claims, 5 Drawing Sheets

U.S. PATENT DOCUMENTS

| | | | |
|---|---|---|---|
| 7,263,164 B2 * | 8/2007 | Ghelmansarai et al. | ........ 378/87 |
| 2008/0146501 A1 | 6/2008 | Hageman et al. | |
| 2008/0246951 A1 | 10/2008 | Walsh et al. | |
| 2008/0280825 A1 | 11/2008 | Hageman et al. | |
| 2009/0048528 A1 | 2/2009 | Hopenfeld et al. | |
| 2010/0140485 A1 * | 6/2010 | Mishra et al. | ............. 250/363.1 |

OTHER PUBLICATIONS

Chen et al., Small-angle scattering computerized tomography (SAS-CT) using a Talbot-Lau interferometer and a rotating anode x-ray tube: theory and experiments, Optics Express, vol. 18, No. 12, pp. 12960-12970.*

Wang et al., Varying Collimation for Dark-Field Extraction, International Journal of Biomedical Imaging, 2009, pp. 1-7.*

International Search Report and Written Opinion, PCT/US2010/037432, Jan. 12, 2011.

Wang, Ge et al., Varying Collimation for Dark-Field Extraction, Accepted Nov. 12, 2009, pp. 1-7, vol. 2009, International Journal of Biomedical Imaging, vol. 2009, Hindawi Publishing Corporation.

Achenbach, S., et al., Contrast-enhanced coronary artery visualization by dual-source computed tomography—Initial experience. European Journal of Radiology, 2006. 57(3): p. 331-335.

Bharkhada, D., et al., Cardiac CT radiation dose reduction using interior reconstruction algorithm with the aorta and vertebra as known information. Journal of Computer Assisted Tomography, 2007. To appear.

Bharkhada, D., et al., Line-source based x-ray tomography. International journal of biomedical imaging, 2009. 2009 (Article ID 534516): p. 8.

Castro, C.R.F., et al., Coherent scattering characteristics of normal and pathological breast human tissues. Radiation Physics and Chemistry, 2004. 71(3-4): p. 649-651.

Chapman, D., et al., Diffraction enhanced x-ray imaging. Physics in Medicine and Biology, 1997. 42(11): p. 2015-2025.

Denis, E., et al., Automatic quality control of digitally reconstructed radiograph computation and comparison with standard methods. Medical Imaging 2007: Physics of Medical Imaging, edited by Jiang Hsieh, Michael J. Flynn, Proc. of SPIE vol. 6510, 65104J.

Fernandez, M., et al., Small-angle x-ray scattering studies of human breast tissue samples. Physics in Medicine and Biology, 2002. 47(4): p. 577-592.

Flohr, T.G.; C. H. McCollough, H. Bruder, M. Petersilka, K. Gruber, C. Süβ, M. Grasruck, K. Stierstorfer, B. Krauss, and R. Raupach, "First performance evaluation of a dual-source CT (DSCT) system," European Radiology, vol. 16, pp. 256-268, 2006.

Guang Yang, et al. Stationary digital breast tomosynthesis system with a multi-beam field emission x-ray source array. in SPIE proceeding on Medical Imaging. 2008.

Hamaker, C. et al., The Divergent beam X-ray transform. Rocky Mountain Journal of Mathematics, 1980. 10(1): p. 253-283.

Johnson, T.R.C., et al., Dual-source CT cardiac imaging: initial experience. European Radiology, 2006. 16(7): p. 1409-1415.

Jung, H., et al., k-t FOCUSS: A general compressed sensing framework for high resolution dynamic MRI. Magnetic Resonance in Medicine, 2008: p. to appear.

Kak, A.C. and M. Slaney, Principles of Computerized Tomographic Imaging. 2001: Society of Industrial and Applied Mathematics.

Kottler, C., et al., Grating interferometer based scanning setup for hard x-ray phase contrast imaging. Review of Scientific Instruments, 2007. 78(4): p. 043710.

Kyriakou Y.; and W. Kalender, "Efficiency of antiscatter grids for flat-detector CT," Physics in Medicine and Biology, vol. 52, pp. 6275-6293, 2007.

LaRoque, S.J., E.Y. Sidky, and X. Pan, Accurate image reconstruction from few-view and limited-angle data in diffraction tomography. Journal of the Optical Society of America A—Optics Image Science and Vision, 2008. 25(7): p. 1772-1782.

Matsumoto, M., et al., Fabrication of diffraction grating for X-ray Talbot interferometer. Microsystem Technologies-Micro-and Nanosystems-Information Storage and Processing Systems, 2007. 13(5-6): p. 543-546.

Momose, A., et al., Biomedical imaging by Talbot-type X-ray phase tomography, in Developments in X-Ray Tomography V, U. Bonse, Editor. 2006, SPIE—Int Society Optical Engineering: Bellingham. p. T3180.

Momose, A., et al., Phase-contrast X-ray computed tomography for observing biological soft tissues (vol. 2, p. 473, 1996). Nature Medicine, 1996. 2(5): p. 596-596.

Momose, A., Recent advances in X-ray phase imaging. Japanese Journal of Applied Physics Part 1-Reg. Papers Brief Comm. & Rev. Papers, 2005. 44(9A): p. 6355-6367.

Orlov, S.S., "Theory of three-dimensional reconstruction. 1. Conditions of a complete set of projections," Sov. Phys. Crystallogr, vol. 20, pp. 312-314, 1975.

Pfeiffer, F., et al., Hard-X-ray dark-field imaging using a grating interferometer. Nature Materials, 2008. 7(2): p. 134-137.

Pfeiffer, F., et al., High-resolution brain tumor visualization using three-dimensional x-ray phase contrast tomography. Phy. in Med. and Bio. 2007. 52(23):p. 6923-6930.

Pfeiffer, F., et al., Phase retrieval and differential phase-contrast imaging with low-brilliance X-ray sources. Nature Physics, 2006. 2(4): p. 258-261.

Poludniowski, G. et al., "An efficient Monte Carlo-based algorithm for scatter correction in keV cone-beam CT," Phys. in Medicine and Biology, vol. 54, pp. 3847-3864, 2009.

Rudin, L. I., S. Osher, et al. (1992). "Nonlinear Total Variation Based Noise Removal Algorithms." Physica D 60(1-4): 259-268.

Sidky, E.Y. C.M. Kao, and X.H. Pan, Accurate image reconstruction from few-views and limited-angle data in divergent-beam CT. Journal of X-Ray Science and Technology, 2006. 14(2): p. 119-139.

Siewerdsen, J. et al., "A simple, direct method for x-ray scatter estimation and correction in digital radiography and cone-beam CT," Medical Physics, vol. 33, p. 187, 2006.

Sprenger, F., et al., Distributed source x-ray tube technology for tomosynthesis imaging. Medical Imaging 2010: Physics of Medical Imaging, edited by Ehsan Samei, Norbert J. Pelc, Proc. of SPIE vol. 7622, 76225M.

Vogel, C.R. and M.E. Oman, Fast, robust total variation-based reconstruction of noisy, blurred images. Ieee Transactions on Image Processing, 1998. 7(6): p. 813-824.

Wang Ge ; Yu Hengyong. Can interior tomography outperform lambda tomography? PNAS (Jun. 1, 2010), vol. 107, Issue 22, pp. E92-E93.

Zitova, et al., Image Registration Methods: A Survey; 24 pgs., Image and Vision Computing 21 (2003) 977-1000.

* cited by examiner

Geometry for Detection of X-ray Scattering Signals

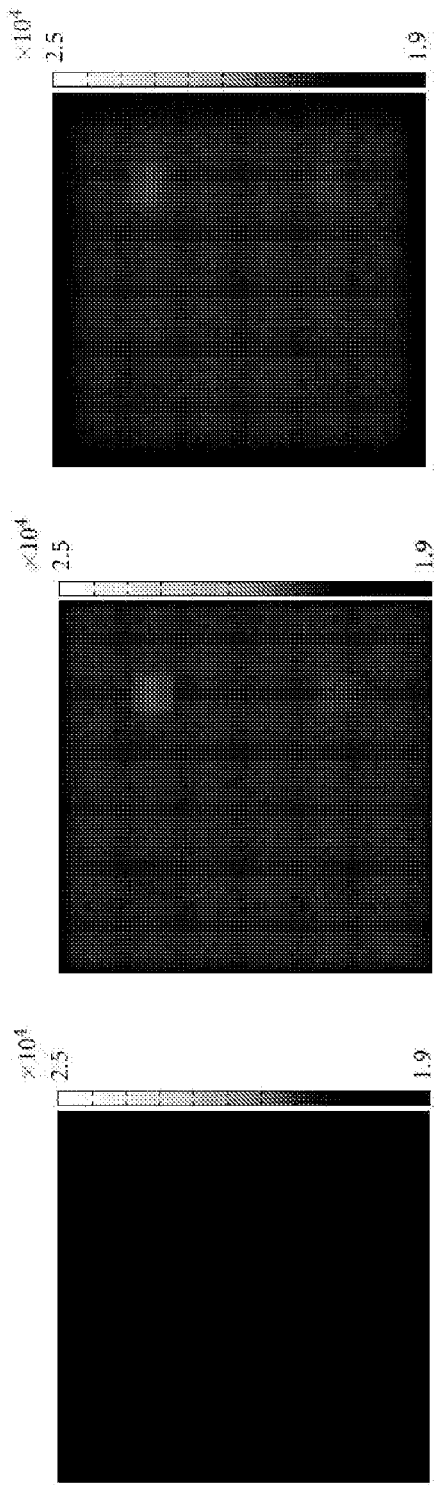
FIG. 4C
FIG. 4B
FIG. 4A
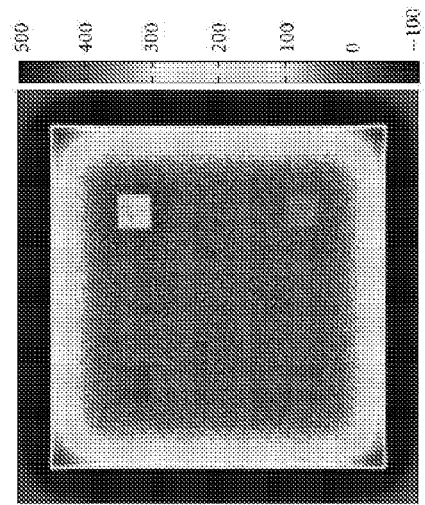
FIG. 4E
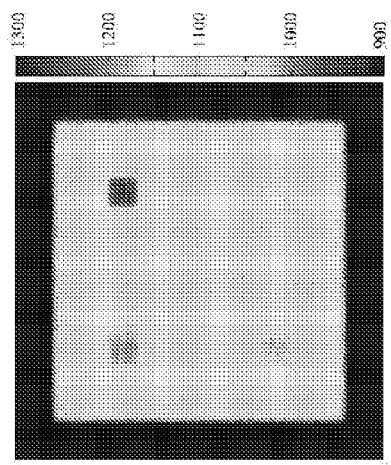
FIG. 4D

MULTI-PARAMETER X-RAY COMPUTED TOMOGRAPHY

CROSS-REFERENCE TO RELATED APPLICATIONS

This application relies on the disclosure of and claims the benefit of the filing date of U.S. Provisional Application No. 61/184,029, filed Jun. 4, 2009, the disclosure of which is incorporated by reference herein in its entirety.

STATEMENT OF GOVERNMENT INTEREST

This work was partially supported by the National Institutes of Health under Grants EB001685, EB006036, EB008476, CA135151 and CA127189. The U.S. Government has certain rights in the invention.

BACKGROUND OF THE INVENTION

1. Field of the Invention

The present invention relates to the field of x-ray imaging. More particularly, embodiments of the invention relate to methods, systems, and apparatus for imaging, which can be used in a wide range of applications, including medical imaging, security screening, and industrial non-destructive testing to name a few.

2. Description of the Related Art

Since its invention in 1973, X-ray computed tomography (CT) has revolutionized medical imaging and become a cornerstone of modern radiology. Improving resolution and reducing dose are two critical factors in biomedical applications and remain the focuses of CT research. With the emergence of multislice spiral CT in 1998, cone-beam scanning is recognized as a major mode for medical CT and widely used in numerous diagnostic and therapeutic procedures. Moreover, the rapid development of small animal models, especially those with genetically engineered mice, has generated the need for preclinical imaging, reaching image resolution in the micron range. These scanners, while producing high spatial resolution images, do not allow high contrast and low dose imaging in either patients or animal models. For example, many normal and diseased tissues such as cancers display poor image contrast in current X-ray images as they have very similar attenuation characteristics.

X-ray mammography is currently the most prevalent imaging modality for screening and diagnosis of breast cancers. The use of mammography results in a 25%-30% decreased mortality rate in screened women, however, a multi-institutional trial funded by the American College of Radiology Imaging Network (ACRIN) suggested that approximately 30% of cancers were not detected by screening mammography, and 70%-90% of biopsies performed based on suspicious mammograms were negative. Some false negative and false positive diagnoses often led to missed cancers and inappropriate biopsies.

Conventional medical x-ray imaging, such as mammography, relies on the attenuation contrast mechanism. Biological soft tissues encountered in clinical and pre-clinical imaging (such as breast tissue, gray-white brain matter, liver, mouse tissues, etc.), however, consist mainly of light elements. As a result, the elemental composition is nearly uniform without much density variation. Because of the insufficient contrast between the healthy and malignant tissues, some early-stage tumors cannot be identified using attenuation contrast imaging. In some cases, the x-ray attenuation contrast is relatively poor and cannot offer satisfactory sensitivity and specificity, a key factor limiting the success rate in diagnosing diseased tissue.

Specifically for diagnosing breast cancer, although X-ray CT of the breast can potentially improve diagnostic accuracy over mammography, the state-of-the-art breast CT scanner is still based on the attenuation mechanism. As a result, the use of breast CT requires an intravenous contrast medium and a high radiation dose, since elemental composition is almost uniform with little density variation in breast tissues. Still, it is rather difficult for breast CT to discern early-stage breast cancers.

Absorption and scattering are two largely independent properties of an object. Generally speaking, each is an important factor in characterizing an object optically. The literature already reported that scattering coefficients contain important physiological and pathological information for cancer screening and other purposes. The x-ray scattering in the biological tissue provides an effective contrast mechanism for x-ray imaging that may well outperform or effectively complement attenuation-based imaging. Scattering-based imaging can improve or enable diagnosis for early-stage cancer, and has widely applications to soft tissue imagings. By reconstructing both absorption and scattering properties, x-ray CT can be elevated to the next level with major healthcare benefits.

Driven by major practical needs for better X-ray imaging, exploration into contrast mechanisms other than attenuation has been active for decades, especially in terms of small angle scattering (essentially, Rayleigh scattering) and refraction of X-rays, which are also known as dark-field and phase-contrast imaging, respectively.

Up to now, X-ray Rayleigh scattering-based imaging has been limited to in vitro studies, incapable of volumetric cone-beam scanning, lack of rigorous reconstruction theory, and made little progress into clinical practice.

Since 2006, grating-based X-ray dark-field and phase-contrast tomography is being developed using a hospital-grade X-ray tube, instead of a synchrotron facility or microfocus tube. More specifically, for example, Pfeiffer and coworkers proposed a grating interferometer technique to produce dark-field images using a hospital-grade x-ray tube. F. Pfeiffer, M. Bech, O. Bunk, P. Kraft, E. F. Eikenberry, Ch. Brönnimann, C. Grünzweig, and C. David, "Hard-X-ray dark-field imaging using a grating interferometer," Nature Materials 7, 134-137 (2008). This technology utilizes the optical interference principles to yield high quality dark-field images. The boundaries and interfaces in the biological tissues produce strong signals in dark-field images, indicating detailed structural contours. Moreover, dark-field images have greater signal-to-noise ratios in soft tissues than bright-field counterparts acquired with the same incident X-ray dose. However, the major problems with this grating-based approach are small sample size, long imaging time, and high fabrication cost.

Such an imaging modality may greatly enhance sensitivity and specificity for soft tissue imaging, revealing subtle structural variation of tissues. However, the data acquisition procedure is quite time-consuming. The gratings with large sizes and high slit aspects are difficult to fabricate and model, especially since the analyzer absorption grating consists of Au pillars encased in epoxy and bounded using a frame.

In 2004, Harding proposed an x-ray coherent scattering imaging method. It uses an x-ray fan-beam to illuminate an object slice for acquisition of coherent scattering data with multiple detector rows. G. Harding, "X-ray scatter tomography for explosives detection," Radiation Physics and Chemistry 71, 869-881 (2004). The central detector row of this technology receives the transmitted radiation while the out-of-center rows record only scattered radiation. The technique is able to perform a rapid scan of the object and provides a significant increment in image contrast for quantitative analyses. However, scattering cross-talks cannot be avoided in this imaging modality and would significantly degrade image quality. Efficient and high-quality acquisition of x-ray small-angle scattering signals is still a challenge.

Further, for example, to perform tomographic imaging from x-ray small-angle scattering signals, Strobl et al. proposed a method to simulate the broadening of the angular distribution of small angle scattering for dark field tomographic imaging. This broadening is related to both microscopic structure and multiple scattering along the path length through a matter. Strobl, M., W. Treimer, and A. Hilger, "*Small angle scattering signals for (neutron) computerized tomography*," Applied Physics Letters, 85, 488-490 (2004); and M. Strobl, C. Grünzweig, A. Hilger, I. Manke, N. Kardjilov, C. David, and F. Pfeiffer "*Neutron dark-field tomography*," Physical Review Letters 101, 123902 (2008).

Harding and coworkers approximate the small-angle scattering propagation as a linear model and directly used the filtered backprojection algorithm to reconstruction scattering contrast images from dark field data. See, G. Harding (2004). However, the propagation of x-ray photons through matter is a complex process, which experiences both absorption and scattering simultaneously. A photon propagation model describes photon interaction with matter, and is essential for tomographic imaging.

Thus what is needed is an imaging modality having sufficient sensitivity and specificity to provide high contrast, high quality x-ray based images. Provided by embodiments of the invention are several novel approaches and associated systems for x-ray small-angle scattering based imaging to produce high-contrast images.

SUMMARY OF THE INVENTION

Provided in embodiments of the invention is a varying collimation methodology and other techniques for extraction of small-angle scattering signals for dark field tomography while traditional attenuation-based tomography can also be simultaneously performed in cone-beam geometry. The projection data acquired with a collimator of a sufficiently high collimation aspect ratio contain mainly the primary beam with little scattering, while the data acquired with an appropriately reduced collimation aspect ratio include both the primary beam and small-angle scattering signals. Analysis of these corresponding datasets will produce desirable dark-field signals, which can be used to reconstruct x-ray small-angle scattering images based on the analytic model of the x-ray dark-field developed by the inventors. The data acquisition scheme can be implemented by modifying the collimation technology. Further, it allows volumetric scanning such as with a circular and spiral trajectory.

Also provided by embodiments of the invention is the ability to achieve x-ray dark-field imaging with a multi-pinhole collimator and an anti-wide-angle scattering collimator to acquire x-ray small angle scattering signals. Source x-ray beams transmit through the multi-pinhole collimator to produce fan-shaped multiple pencil beams well separated from each other. One-to-one correspondence between pencil beams and detector elements is established to ensure the small-angle scattering photons generated from each pencil beam propagate toward its corresponding detector element center. The size of a detector element will be larger than that of a common CT detector for acquiring enough small-angle scattering information. An anti-scattering grid is placed in front of detectors to filter out wide-angle scattering photons and allow for small-angle scattering photons to reach its corresponding detector element from each pencil beam. The large size detector element helps fabricate a sufficiently high anti-wide-angle scattering grid to eliminate the cross-talk among scattering signals. The low-resolution induced from larger detectors can be compensated by continuously rotating the detector ring and the source collimator in the range of two neighboring pencil beams to increase the angular sampling rate and enhance the dark-field image resolution. This scheme can acquire high-quality x-ray small-angle scattering signals, allowing a significant reduction of the x-ray dose.

More specifically, provided by embodiments of the invention is an x-ray small-angle scattering photon transport model for development of novel algorithms to reconstruct 3D scattering images. The reconstruction procedure can be effectively implemented with computational complexity comparable to that of conventional attenuation-based CT algorithms.

Generally provided by embodiments of the invention are varying collimation schemes to extract dark-field signals. In embodiments, acquiring x-ray projection data multiple times with varying collimation is a key feature of obtaining high quality, high contrast images.

Embodiments of the present invention provide detection methods for extracting dark-field x-ray small-angle scattering signal data. The projection data acquired with a collimator of a sufficiently high collimation aspect ratio contain mainly the primary beam with little scattering, while the data acquired with an appropriately reduced collimation aspect ratio include both the primary beam and small-angle scattering signals. Analysis of these corresponding datasets will produce desirable dark-field signals, for example, by way of digital subtraction. The acquired extracted dark field signals can clearly reveal the structural information of tissues (or any object subject to the imaging) in terms of Rayleigh scattering characteristics.

Embodiments further provide methods for producing an x-ray image comprising: a) providing at least one first dataset of primary x-ray signals as a majority of its data capable of being presented as a first image of an object subjected to x-ray imaging; b) providing at least one second dataset comprising dark-field x-ray signals and primary x-ray signals as a majority of its data capable of being presented as a second image of the object; c) combining the first dataset and the second dataset using a computer comprising a computer readable medium embedded with processing means for obtaining a target dataset having more dark-field (small-angle scattering) x-ray signals than the first or second dataset alone for producing a target image of the object which has higher contrast quality than the images based on the first or second dataset alone.

Such methods can comprise providing the data using collimator-and-detector assemblies or configurations that differ with respect to collimator height, collimator aperture, imaging geometry, or distance between an object subjected to the imaging and the collimator-and-detector assembly.

Extracting the dark-field signal data can be performed using a computer and computer readable medium embedded with processing means is based on: a) Radon transform with respect to a small-angle scattering coefficient distribution derived from the principle of photon energy conservation:

$$\ln\left[1 + \frac{\Phi_s(r_0 R\theta)}{\Phi_a(r_0 R\theta)}\right] = \int_0^R \mu_s(r_0 + s\theta)ds \quad (9.1)$$

where $\Phi_a(r_0+R\theta)$ is intensity of transmission photon and $\Phi_s(r_0+R\theta)$ is intensity of small-angle scattering photons on a detector, and Eq. (9.1) can be normalized as $$\ln\left[1 + \frac{T_s(r + R\theta)}{T_a(r + R\theta)}\right] = \int_0^R \mu_s(r + s\theta)ds \quad (9.2)$$

where $$T_a(r + R\theta) = \frac{\Phi_a(r + R\theta)}{\Phi_0} \text{ and } T_s(r + R\theta) = \frac{\Phi_s(r + R\theta)}{\Phi_0}$$

are the photon transmission and small-angle scattering transference, respectively, and $\Phi_0$ is the intensity of incident x-ray, and where Eq. (9.2) describes the relationship between the small-angle scattering coefficient, measured photon transmission and small-angle scattering transference; or b) another governing equation derived from the radiative transfer equation (RTE); or c) another approximation to the radiative transfer equation (RTE).

Methods of the invention can further comprise a computer readable medium embedded with processing means for performing x-ray dark-field tomography (XDT) from the extracted dark-field x-ray data.

Embodiments of the invention provide systems system for x-ray imaging comprising: a) a first collimator-and-detector assembly having a first operable configuration to provide at least one first dataset comprising primary x-ray signals as a majority of its data capable of being presented as a first image of an object subjected to x-ray imaging; b) a second collimator-and-detector assembly having a second operable configuration or wherein the first collimator-and-detector assembly is adjustable to a second configuration to provide at least one second dataset comprising primary and dark-field x-ray signals as a majority of its data capable of being presented as a second image of the object; c) a computer operably coupled with the collimator-and-detector assemblies comprising a computer readable medium embedded with processing means for combining the first dataset and the second dataset to extract the dark-field x-ray signals and produce a target image having higher contrast quality than the images based on the first or second dataset alone.

System embodiments of the invention can comprise systems having at least two of the collimator-and-detector assemblies or configurations differ with respect to collimator height, collimator aperture, imaging geometry, or distance between an object subjected to the imaging and the collimator-and-detector assembly.

Further included are system embodiments wherein the computer readable medium embedded with processing means is based on: a) the analytic model of x-ray dark-field described above, or b) another governing equation derived from the radiative transfer equation (RTE); or c) another approximation to the radiative transfer equation (RTE).

Systems embodiments further include systems with a computer readable medium embedded with processing means for performing x-ray dark-field tomography (XDT) from the extracted dark-field x-ray data.

Also encompassed by embodiments of the invention are methods of x-ray imaging comprising: a) collecting x-ray data with a collimator-and-detector assembly configured to provide at least one first dataset comprising primary x-ray signals as a majority of its data; b) adjusting the collimator-and-detector assembly to a second configuration for collecting at least one second dataset comprising primary and dark-field x-ray signals as a majority of its data or collecting the second dataset with a second collimator-and-detector assembly configuration; and c) computing the first and second datasets with a computer operably coupled with the collimator-and-detector assembly and comprising a computer readable medium embedded with processing means for extracting the dark-field x-ray signals for producing a target image having a higher contrast quality than an image based on the first or second dataset alone.

Such methods can further comprise collecting x-ray data with additional collimator-and-detector assemblies or additional collimator-and-detector adjustments and computing two or more of the datasets to extract the dark-field signals for producing an image.

Methods of embodiments of the invention can comprise employing at least two of the collimator-and-detector assemblies or adjustments differ with respect to collimator height, collimator aperture, imaging geometry, or distance between an object subjected to the imaging and the collimator-and-detector assembly.

These methods can involve detecting x-ray photons in a spectrally resolving fashion, or at least one collimator-and-detector assembly or adjustment is configured to detect Compton scattering photons in a spectrally resolving fashion.

Such methods can involve employing at least one collimator-and-detector assembly or adjustment configured to allow fan-beam or cone-beam scanning along a general trajectory, including a circular or spiral loci.

Embodiments of methods of the invention can include performing computations by way of a computer readable medium embedded with processing means based on: a) the analytic model of x-ray dark-field described above; or b) another governing equation derived from the RTE equation; or c) another approximation to the RTE equation.

Methods and systems according to embodiments of the invention can be configured or performed to obtain a target image based on the extracted dark-field x-ray data that is produced in a radiographic/2D mode. Likewise, a tomographic or stereographical or tomosynthesis mode can also be used.

Methods and systems of the invention can further comprise performing x-ray dark-field tomography (XDT) and Compton scattering imaging from the extracted spectral x-ray data. Such embodiments can include performing x-ray dark-field tomography (XDT) from the extracted dark-field data to characterize small-angle scattering properties in terms of one or more parameters, or to characterize small-angle scattering properties in terms of Rayleigh scattering coefficient, or to characterize Rayleigh scattering phase function.

BRIEF DESCRIPTION OF THE DRAWINGS

FIGS. 4A-E provide several images showing the differences between images obtained by varying parameters of the system, including collimation aspect ratios and object-detector distance, as well as images produced by combining the various results.

DETAILED DESCRIPTION OF VARIOUS EMBODIMENTS OF THE INVENTION

Reference will now be made in detail to various exemplary embodiments of the invention. The following detailed description is presented for the purpose of describing certain embodiments in detail and is, thus, not to be considered as limiting the invention to the embodiments described.

Included in embodiments of the invention are methods for extracting x-ray small-angle scattering data and using this segregated data to produce a high quality, high contrast x-ray image. A technique for extracting the x-ray small-angle scattering data involves collecting the x-ray projection data multiple times with varying collimation before an x-ray detector array. In preferred embodiments, each x-ray sum is acquired at least twice using different collimation aspect ratios. The projection data acquired with a collimator of a sufficiently large aspect ratio (otherwise referred to as a high collimation aspect ratio) contain mainly the primary beam with little scattering. In contrast, the corresponding data acquired with an appropriately reduced collimation aspect ratio (otherwise referred to as a small or low collimation aspect ratio) include both small-angle scattering signals and the primary beam signals. Analysis of these paired or corresponding datasets (e.g., by digital subtraction of one dataset from the other) will produce or isolate the desired dark-field signals, in addition to traditional transmission measurement.

Conventionally, an anti-scattering grid is coupled with an area detector to eliminate x-ray scattering photons. The intensity of scattered radiation into a detector cell is determined by the height of the anti-scattering grid. The lower the height of the anti-scattering grid is, the more the scattered photons enter the detector cell. The height of the anti-scattering grid is typically selected to reject scattered photos as much as feasible subject to the cost associated with the fabrication process.

In embodiments of the invention, and depending on a specific imaging application, the height of the anti-scattering grid can be selected appropriately so that only the primary and small-angle scattering signals are intercepted. The resultant projection is denoted as PS. Then, the height of the anti-scattering grid can be increased significantly so that small-angle scattering signals are also rejected to acquire essentially only the transmission data. The corresponding projection is denoted as PT. Hence, the difference between PS and PT is understood to be closely correlated to the desirable small-angle scattering signals.

Figure 1:
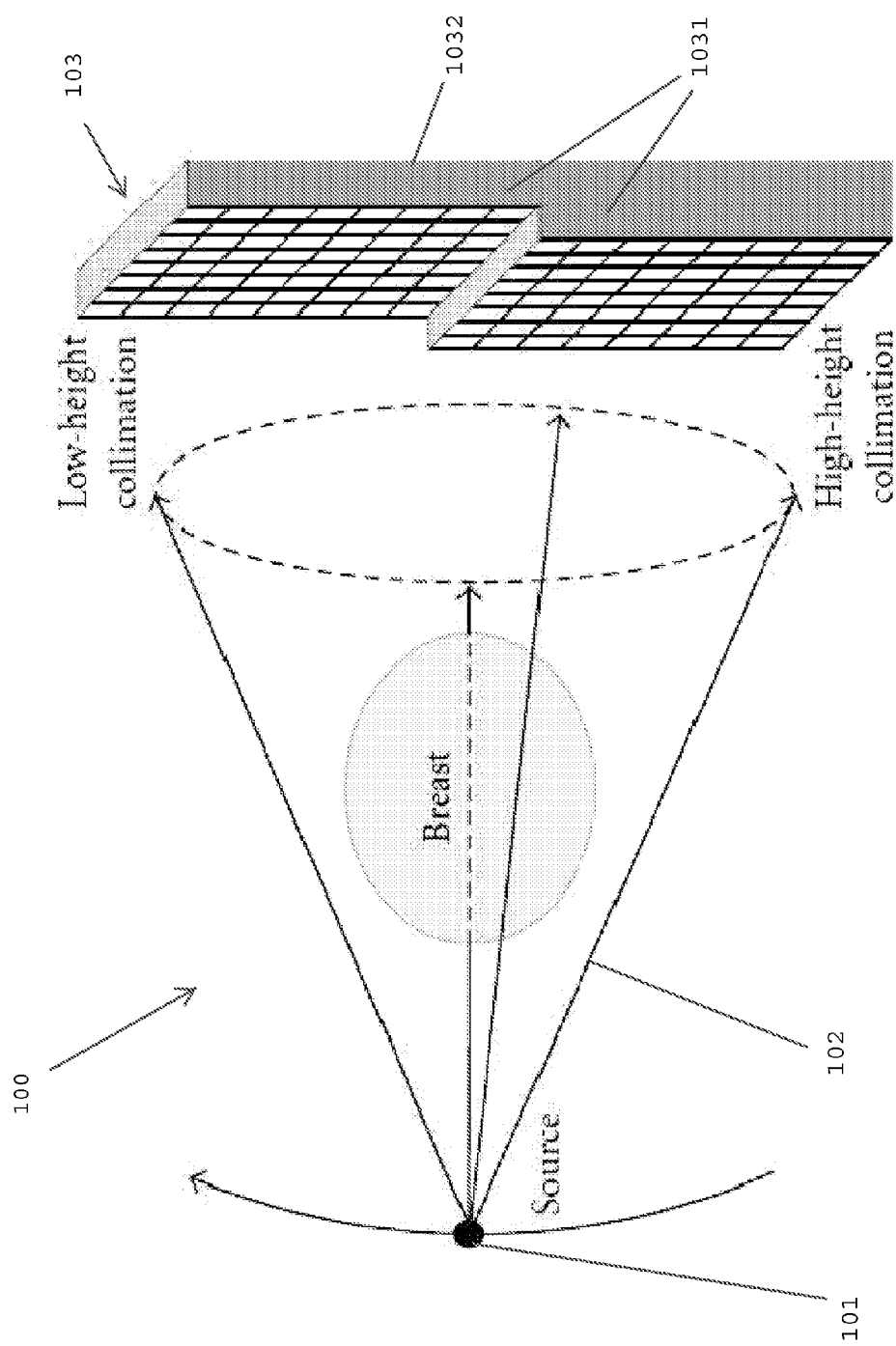
FIG. 1 provides a schematic diagram of one variation of the varying collimation approach according to embodiments of the present invention.

FIG. 1 provides a schematic diagram of one variation of the varying collimation approach, which can be accomplished in numerous ways. For example, the varying collimation approach does not necessarily require two pass scans with different collimation aspect ratios. Provided is an example of a single pass cone-beam circular scan with a dual collimation detector array for both dark-field tomography and transmission x-ray CT.

More specifically, as shown in FIG. 1, an imaging system 100 according to embodiments of the invention comprises an x-ray source 101 for producing and directing an x-ray beam 102 through an object of interest and a collimator-and-detector assembly 103 for receiving and detecting the x-ray projection data. One embodiment can include use of a dual-height collimator 1031 in combination with a 2D detector array 1032. In such a configuration, as shown, a circular cone-beam full-scan can be performed in combination with a dual-height collimator, for example, disposed in front of a 2D detector array.

In this setting, on the mid-plane each pixel on a given line is irradiated by two and only two x-rays along that same line but with two different collimation heights in the opposite directions respectively, sufficient for extraction of dark-field signals. It is underlined that scatter intensities measured in opposite directions in one full-scan are different from that measured in the same direction with two full-scans, since dark field integrals along the same line are generally asymmetric. Nevertheless, this type of difference can be well modeled and calibrated by the governing equation modified Leakeas-Larsen equation (MLLE), and then, for example, a generalized Feldkamp-type dark-field cone-beam reconstruction can be performed from the resultant dataset. It is possible to apply this technology to other cone-beam scanning trajectories, which could lead to other useful cone-beam algorithms. Actually, varying collimation gives us a new dimension to analyze scattering signals. We may use two or more collimation aspect ratios, depending on specific imaging requirements. It is also possible to have different varying collimation designs, for example, by changing the size of collimators for a fixed collimation height, implementing various collimation aspect ratios. Also, it is possible to vary the x-ray tube voltage or imaging geometry for more information.

X-ray single scattering model. While an x-ray pencil beam propagates along a straight line, this beam would become a source of photon scattering in an object being imaged. The number of scattered photons is directly related to density of matter, which can be quantified by the scattering coefficient. The x-ray scattering tomographic imaging is to reconstruct the scattering coefficient distribution in the object. The intensity distribution of photon scattering sources on this x-ray beam line can be expressed as:

$$Q(\theta, d, r) = I_0 \exp\left(-\int_0^{l_r} \mu_t(s_0 + l\theta) dl\right) \quad (1)$$

where $\theta$ is a projection angle, and d is the distance from the origin to the pencil beam meeting $\theta \cdot r = d$, and $r = s_0 + l_r \theta$.

Small-angle and large angle x-ray scattering signals come essentially from the coherent scattering (Rayleigh scattering) and incoherent scattering (Compton scattering) mechanisms, respectively. Compton scattering describes the interaction of a photon with an electron in an outer shell of an atom. A fraction of the x-ray energy is transferred to the electron. While the electron is ejected, the x-ray photon is deflected from its original path. The probability for an incoming photon with energy $E_\gamma$ being scattered in a direction $\phi$ can be described by the Klein-Nishina formula:

$$p_c(\phi) = \frac{r_e^2}{2[1 + \alpha(1 - \cos\phi)]^2} \cdot \left[1 + \cos^2\phi + \frac{\alpha^2(1 - \cos\phi)^2}{1 + \alpha(1 - \cos\phi)}\right] \quad (2)$$

where $\alpha = E_\gamma/m_e c^2$, $m_e$ is the electron mass, c the speed of light, $r_e$ the classical radius of electron, and $n_e(\vec{r})$ the free electron density.

Rayleigh scattering represents non-ionizing interactions between x-rays and matters. It is an elastic scattering process. The scattered photons have the same energy as the incident photons. The differential cross-section of Rayleigh scattering or the probability of a photon scattering into a given angle $\phi$ is described by:

$$p_r(\phi) = \frac{r_e^2}{2}(1+\cos^2\phi)F^2(\phi, E_\gamma, Z) \quad (3)$$

where $F(\theta, E_\gamma, Z)$ is the atomic form factor. Since the form factor is highly complex, most x-ray Monte Carlo simulators use a database to store the form factor data. The form factor can be approximated with the simple function: $F(\theta, E, Z) = c_1 \theta^j e^{-c_2\theta}$.

The combined differential cross-section per atom can be expressed as:

$$p(\phi) = p_r(\phi) + N_e p_c(\phi) \quad (4)$$

where $N_e$ is the number of free electrons in the atom.

The scattering-induced linear attenuation coefficient can be defined as:

$$\mu_s = 2\pi n_s \int_0^\pi d\theta p'(\theta) = n_s \sigma_s, \quad (4a)$$

where $n_s$ indicates the number density of scatter atoms, and $$\sigma_s = 2\pi \int_0^\pi d\theta p'(\theta)$$

indicates the total scatter cross section. The combined probability of Rayleigh and Compton scattering then becomes:

$$p(\theta) = \frac{1}{\sigma_s} p'(\theta). \quad (4b)$$

The total Rayleigh probability can be defined as $$\beta = \frac{\sigma_r}{\sigma_s},$$

where $$\sigma_r = 2\pi \int_0^\pi d\theta p_r(\theta).$$

The number of scattered photons detected by detectors can be expressed as:

$$D(\theta, d) = \int\int \left[\int_{\phi_1 \leq \phi \leq \phi_2} p(\phi) \exp\left(-\int u_t(r+s\phi)ds\right) d\phi\right] Q(\theta, d, r)\mu_s(r) dr \quad (5)$$

wherein $\phi_1$ and $\phi_2$ are the low and up bounds of scattering angles at position r, which are a function of the size of the detector and the detector to object distance.

The attenuation coefficients $\mu_t$ in Eq. (5) can be obtained from attenuation-based computed tomography (CT). Hence, Eq. (3) is a linear integral equation with respect to scattering coefficient $\mu_s$, which can be discretized as a system of linear equations:

$$A \cdot S = b, \quad (6)$$

where S is the discretized vector of scattering coefficient, and b the measured number of scattering photons.

Compressive sensing (CS) theory asserts that one can reconstruct images with a sparse representation from far less samples or data than what the Nyquist sampling theorem demands. The success of CS relies on both the sparsity of an underlying image and the incoherence of the sensing matrix. Compressive sensing techniques can be used to perform the scattering image reconstruction based on Eq. (6). The high order TV (HOT) approach was recently developed for interior tomography. See, Yang J, Yu H, Jiang M, Wang G (2010), High order total variation minimization for interior tomography. Inverse Probl, 10.1088/0266-5611/26/3/035013, which is hereby incorporated by reference herein in its entirety. This approach can be used as a criterion for dark-field tomography. Statistical optimization methods can also be used for this purpose.

Single Scattering Method. A single scattering model in 3D can be used to demonstrate the varying height collimation technology. Although other models would be equally applicable, the single scattering model represents the simplest x-ray scattering scenario.

Figure 2:
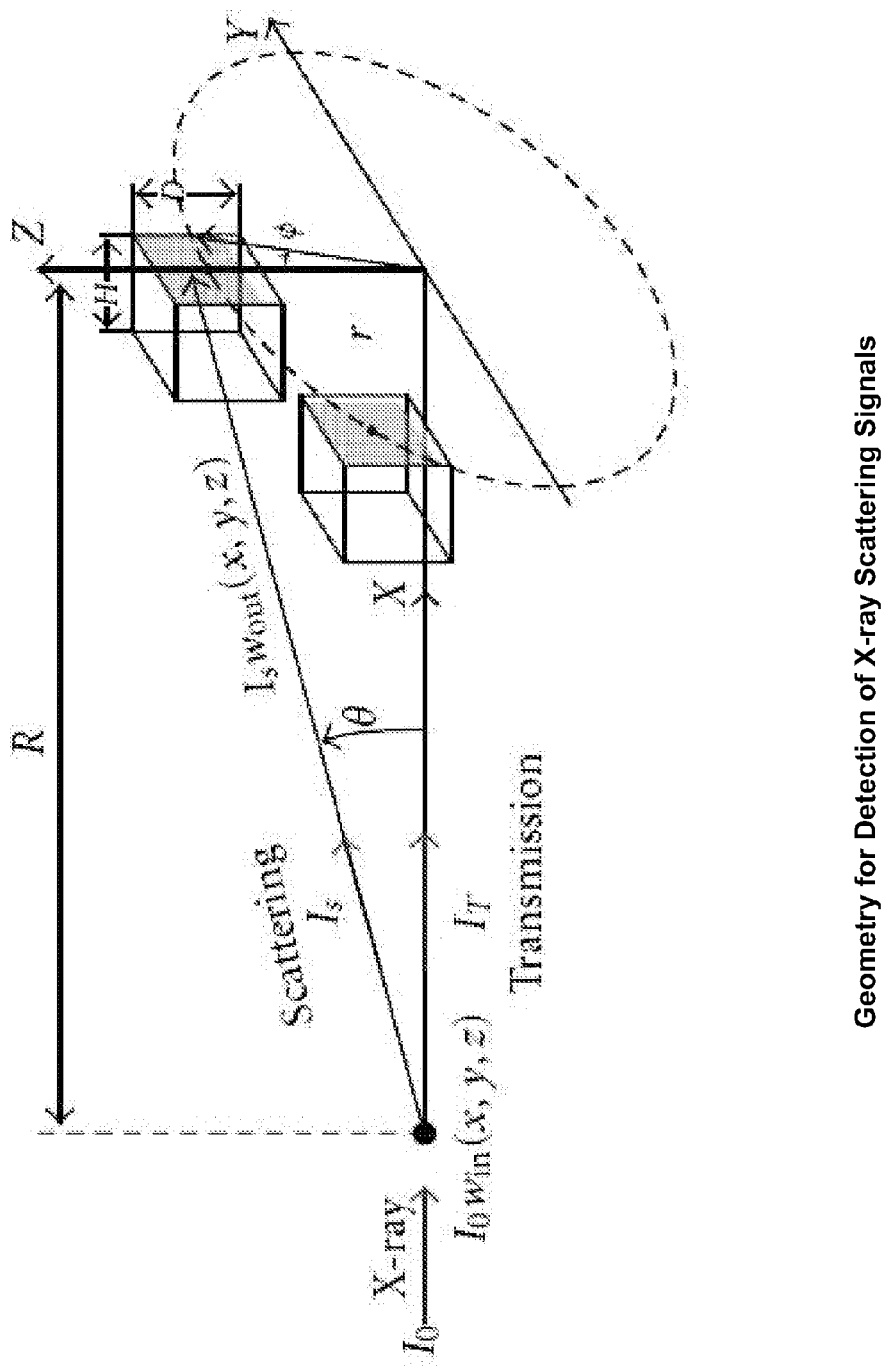
FIG. 2 provides a schematic diagram illustrating the geometry for detection of x-ray scattering signals.

FIG. 2 provides a schematic diagram illustrating the geometry for detection of x-ray scattering signals. As shown in FIG. 2, the x-ray scattering intensity into a detector cell can be expressed as:

$$f(H) = \frac{1}{2\pi}\int dz \int dy \int dx I_0 w_{in}(x, y, z) \quad (6a)$$
$$w_{out}(x, y, z)\mu_s(x, y, z) \int_{\varphi_1}^{\varphi_2} d\varphi \int_{\theta_1}^{\theta_2} d\theta p(\theta)$$

where $$\frac{1}{2\pi}\int_{\varphi_1}^{\varphi_2} d\varphi \int_{\theta_1}^{\theta_2} d\theta p(\theta)$$

is the probability that a scattered photon hits a target detector pixel, $I_0$ the source intensity, $w_{in}(x,y,z)$ the source attenuation factor, $w_{out}(x,y,z)$ the scattering signal attenuation factor which also depends on the location of the detector cell, and $\mu_s(x,y,z)$ the scattering coefficient. As shown in FIG. 2, $p(\theta)$ represents a symmetry distribution around the incoming direction of a photon. Hence, when compute the differential solid angle extended by a detector cell we can always rotate the detector cell such that its center is on the X-Z plane for easy computation. Generally speaking, the following limits can be used to compute this probability approximately:

$$\begin{cases} \theta_1 = \arctan\left(\frac{r - D/2}{R - H}\right), & \theta_2 = \arctan\left(\frac{r + D/2}{R}\right) \\ \varphi_1 = -\arctan\left(\frac{D/2}{r}\right), & \varphi_2 = \arctan\left(\frac{D/2}{r}\right) \end{cases} \quad (6b)$$

where H is the grid height, D the aperture of the detector cell, and R the distance from a scattering location to the detector cell. Note that the scattering behavior $$\frac{1}{2\pi}\int_{\varphi_1}^{\varphi_2}d\varphi\int_{\theta_1}^{\theta_2}d\theta_p(\theta)$$

can be analytically computed, numerically estimated, or statistically simulated.

X-ray small-angle scattering equation. In quantum mechanics, light is considered with both wave and particle behaviors. Hence, the x-ray photon transmission can be treated as a beam of particles propagating through an object. As x-ray photons interact with the object, some photons would be deflected from the original direction due to a difference in the refractive index and generate a scattering signal. Thus, x-ray photons can be divided into transmitted photons traveling along a straight line in a direction θ and scattered photons deflected from the original direction. The propagation of transmitted photons along the direction θ can be well described by the Beer-Lambert law:

$$\Phi_a(r_0 + R\theta) = \Phi_a(r_0 + t\theta)\exp\left(-\int_t^R \mu_t(r_0 + s\theta)ds\right) \quad (7)$$

where $\Phi_a(r_0+t\theta)$ is the light intensity along the direction θ, and $\mu_t$ the attenuation coefficient defined as a sum of absorption coefficient $\mu_a$, wide-angle scattering coefficient $\mu_w$ and small-angle scattering coefficient $\mu_s$, that is, $\mu_t=\mu_a+\mu_w+\mu_s$. Eq. (7) can be reduced to a Radon transform:

$$\ln\left[\frac{\Phi_a(r+t\theta)}{\Phi_a(r+R\theta)}\right] = \int_t^R \mu_t(r+s\theta)ds \quad (8)$$

where $\Phi_a(r_0+t\theta)$ and $\Phi_a(r_0+R\theta)$ express the intensity of transmitted photons at position r+tθ and r+Rθ, respectively.

While an x-ray beam propagates along a straight line, some photons would experience a small-angle forward scattering. The so-called dark-field image is formed through the small-angle scattering of x-rays. The small-angle scattered photon intensity $\Phi_s(r)$ depends on both absorption and scattering properties of an object. According to the energy conservation principle, the difference $d\Phi_s(r)$ of the small-angle scattered photon intensity between the opposite sides of an elementary volume with a cross sectional area dA and length dh along the direction θ is equal to the difference between intensity of small-angle scattered photons from the primary beam and the sum of the intensities of photons absorbed and wide-angle scattered by the object, which can be expressed as follows:

$$d\Phi_s(r)dA = \mu_s dh\Phi_a(r)dA - (\mu_a+\mu_w)dh\Phi_s(r)dA \quad (9)$$

Since $d\Phi_s(r)dA=\theta\cdot\nabla\Phi_s(r)dhdA$, a differential equation in terms of the small-angle scattered photon intensity can be established from Eq. (9):

$$\theta\cdot\nabla\Phi_s(r)dA+(\mu_a+\mu_w)\Phi_s(r)=\mu_s\Phi_a(r) \quad (10)$$

where $(\mu_a+\mu_w)\Phi_s(r)$ represents the loss of the small-angle scattering intensity due to photoelectric absorption and wide-angle scattering, and $\mu_s\Phi_a(r)$ is the quantity of small-angle scattered photons from the primary beam $\Phi_a(r)$. In other words, Eq. (10) describes the balance of the photons between the input and output of an elementary volume at the given direction θ. Because Eq. (10) is a linear first-order differential equation, its solution can be obtained in the closed form:

$$\Phi_s(r + R\theta) = \quad (11)$$
$$\int_0^R \mu_s(r+t\theta)\Phi_a(r+t\theta)\exp\left(-\int_t^R[\mu_a(r+s\theta)+\mu_w(r+s\theta)]ds\right)dt$$

Substituting Eq. (7) into Eq. (11), the following equation is obtained:

$$\Phi_s(r_0+R\theta)=\Phi_a(r_0+R\theta)\int_0^R \mu_s(r_0+t\theta)\exp\left(\int_t^R \mu_s(r_0+s\theta)ds\right)dt \quad (12)$$

Using a variable transformation, Eq. (12) can be simplified to a Radon transform with respect to the small-angle scattering coefficient distribution:

$$\ln\left[1+\frac{\Phi_s(r_0+R\theta)}{\Phi_a(r_0+R\theta)}\right]=\int_0^R \mu_s(r_0+s\theta)ds \quad (13)$$

where $\Phi_a(r_0+R\theta)$ and $\Phi_s(r_0+R\theta)$ are the intensity of transmission photon and the intensity of small-angle scattering photons on the detectors, respectively. Eq. (13) can be normalized as $$\ln\left[1+\frac{T_s(r+R\theta)}{T_a(r+R\theta)}\right]=\int_0^R \mu_s(r+s\theta)ds \quad (14)$$

where $$T_a(r+R\theta)=\frac{\Phi_a(r+R\theta)}{\Phi_0} \text{ and } T_s(r+R\theta)=\frac{\Phi_s(r+R\theta)}{\Phi_0}$$

are the photon transmission and small-angle scattering transference, respectively, and $\Phi_0$ is the intensity of incident x-ray. Eq. (14) describes the relationship between the small-angle scattering coefficient, measured photon transmission and small-angle scattering transference. Eq. (14) is also a standard Radon transform for the small-angle scattering coefficient, so classical reconstruction algorithms, such as the filtered backprojection (FBP) algorithm and algebraic reconstruction technique (ART), can be applied to reconstruct the small-angle scattering coefficient distribution tomographically.

Monte Carlo Simulation Method. There exists a tetrahedron-based inhomogeneous Monte-Carlo optical simulator (TIM-OS) for optical light propagation in complex biological tissue. The core of this simulator is a fast propagation algorithm, which can move particles efficiently in complex geometry represented by tetrahedron finite element mesh. The TIM-OS framework was migrated for x-ray simulation to take advantage of the great speedup in optical simulation that can be achieved with this framework.

X-ray and matter interaction is very complex in general. In this prototype MC x-ray simulator, a simplified x-ray-matter interaction model was considered to cover the three major components in dark-field imaging: Photoelectric effect (absorption), Rayleigh scattering, and Compton scattering.

Three parameters were used to describe the x-ray-matter interaction: absorption coefficient ($\mu_r$), scattering coefficient ($\mu_s$), and Rayleigh percentage ($\beta$).

The definition of absorption coefficient is the probability of x-ray absorption per unit path length. The scattering coefficient is the probability of an x-ray photon involved in scattering (Rayleigh or Compton scattering) per unit path length. Rayleigh percentage determines the likelihood both Rayleigh and Compton scattering.

After an x-ray photon is launched, a routine will be followed to find out the entering point of the photon into the phantom. While the photon is in the phantom, a step size will be generated based on the local absorption and scattering coefficients as $s=-\ln(\xi)/(\mu_r+\mu_s)$, where $\xi$ is an uniform random number from region (0,1). If this photon needs to go across several different regions, the total step size $s=\Sigma_i s_i$ is governing by the following equation: $\Sigma_i(\mu_{r\_i}+\mu_{s\_i})s_i=-\ln(\xi)$. After the photon moves the free fly step, the photon will be absorbed or scattered based on the ratio of the absorption coefficient and scattering coefficient. If the photon is absorbed, the program will launch a new photon; otherwise, the photon is scattered.

According to $\beta$, the photon scattering will be governed by either the Rayleigh or Compton mechanism. Then, the scattering angle will be found according to the corresponding form factor. Then, the photon will be assigned another step size based on the current local x-ray parameters. These steps will be repeated until the photon moves out of the phantom.

Voxel-based and surface-based schemes are two of the most popular techniques employed in x-ray simulation to deal with a complex geometry. The surface-based scheme uses a triangle mesh to represent the interface between two regions and the surface. In this case, a simulation program needs to determine whether the involved photon moment will hit a triangle for each step. Given a complex geometry, the photon-triangle interaction could be very slow. The voxel-based scheme directly uses a CT reconstruction volume to represent geometry. This may introduce a huge computational overhead when a high-resolution volumetric image is used. The key idea underlying this tetrahedron-based scheme is that by modeling an object as a tetrahedron-based finite element mesh, TIM-OS can specify the photon-triangle interaction rapidly and recursively. In other words, since a photon starts its movement inside a tetrahedron, the ray-triangle interaction would only happen with one of the four triangles of the tetrahedron, reducing the searching space significantly.

Simulation Result. Monte Carlo simulation was used to verify the varying collimation scheme and compare the single scatter method with Monte Carlo simulation result.

Figure 3:
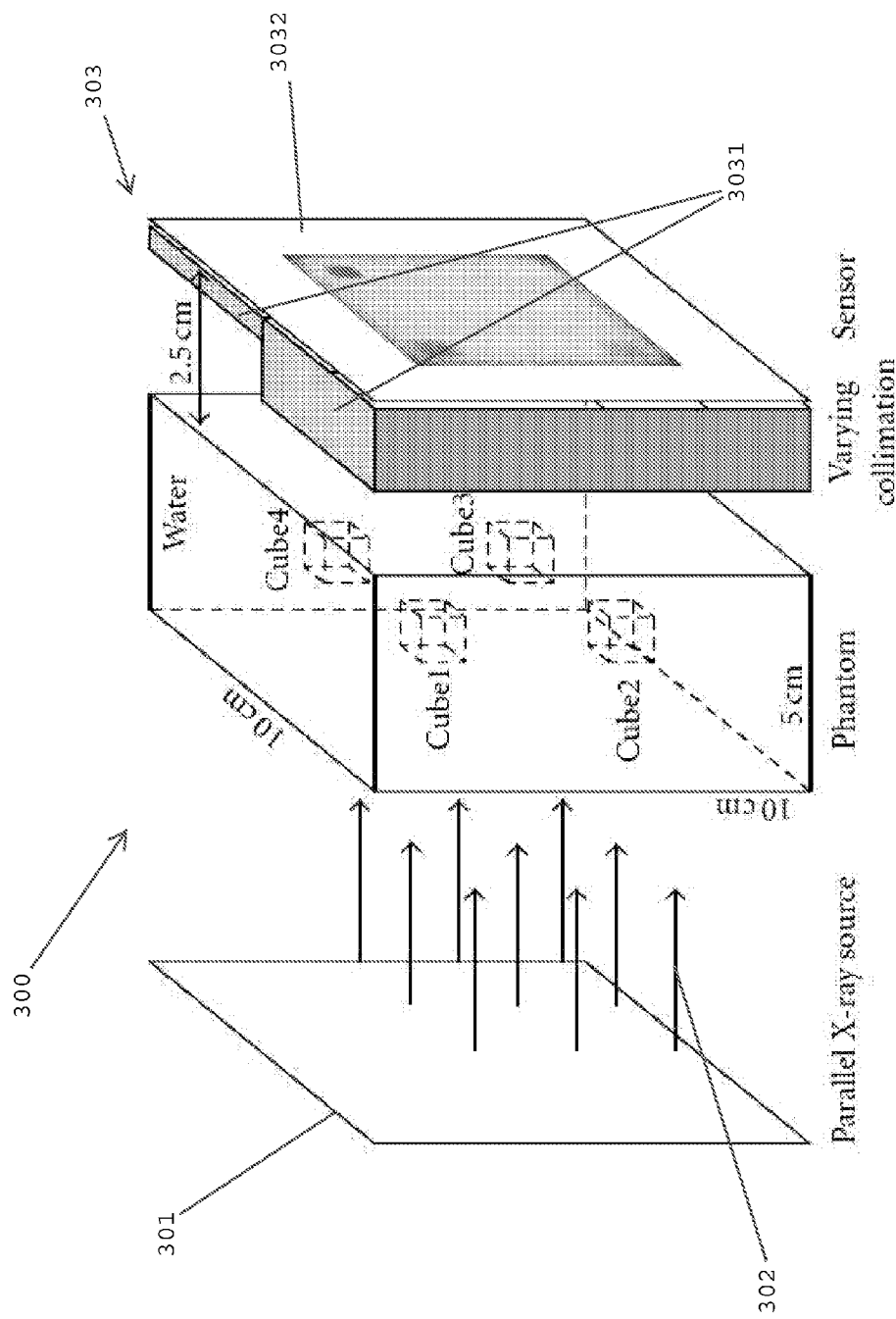
FIG. 3 provides a schematic diagram illustrating small-angle scattering simulation.

FIG. 3 provides a schematic diagram illustrating small-angle scattering simulation. As shown in FIG. 3, the simulation setting, which forms a basic construct for methods and systems 300 of the invention, included a 10×10×5 cm³ phantom (object subjected to imaging) with four 1 cm cubic sub-regions (internal objects of interest). The phantom material was set to water. Furthermore, the four cubic sub-regions were made of the same attenuation coefficient as water but with different scattering behaviors.

According to literature, at 50 KeV water's total attenuation coefficient is 0.21(cm$^{-1}$). In the attenuation coefficient, the absorption is about 13.3% (0.028 cm$^{-1}$), the Rayleigh scattering ($\mu_{s\_r}$) is 6.7% (0.014 cm$^{-1}$), and Compton scattering ($\mu_{s\_a}$) is 80% (0.168 cm$^{-1}$). Two of the cubes had lower Rayleigh scattering coefficients, and the other two had higher Rayleigh scattering coefficients.

Table III lists the x-ray absorption and scattering coefficients at 50 KeV of the phantom components.

TABLE III

X-ray absorption and scattering coefficients at 50 KeV of the phantom components.

| Material | Absorption Coefficient (cm$^{-1}$) | Scattering Coefficient ($\mu_s = \mu_{s\_r} + \mu_{s\_c}$) (cm$^{-1}$) | | |
|---|---|---|---|---|
| | | $\mu_{s\_r}$ | $\mu_{s\_c}$ | $\mu_{s\_r}/(\mu_{s\_r}+\mu_{s\_c})$ |
| Water | 0.028 | 0.0140 | 0.1680 | 0.0769 |
| Cube 1 | 0.028 | 0.0035 | 0.1785 | 0.0193 |
| Cube 2 | 0.028 | 0.0070 | 0.1750 | 0.0385 |
| Cube 3 | 0.028 | 0.0260 | 0.1560 | 0.1429 |
| Cube 4 | 0.028 | 0.0520 | 0.1300 | 0.2858 |

A parallel x-ray source 301 was used to provide x-ray beams 302 through the phantom subjected to imaging for detection by a collimator-and-detector assembly 303. The pixel size of the detector 3032 was set to 0.2×0.2 mm² and there were a total of 600×600 pixels to cover the whole phantom area. The distance between the phantom and the detector plane 3032 was 2.5 cm. In system and method embodiments of the invention, the distance between the object being imaged (here, the phantom) can be varied to achieved different collimation heights. In this simulation, a dual-height collimator 3031 was used.

For example, any distance between the object subjected to imaging and the detector (sensor) can be used depending on a particular application. Likewise, varying collimation heights can also be achieved by varying distance between the x-ray beam source and the detector regardless of where the object being imaged is disposed between the source and the detector. Providing exact distance dimensions would not be appropriate in this situation, as depending on a particular application, actual dimensions may or may not be relevant. What is important with respect to varying the distance between the source and the detector or varying the distance between the detector and the object being imaged is the change in distance from one imaging configuration to another.

Further, for example, to vary collimation height from one imaging scenario using a particular collimator-and-detector assembly configuration with a set collimator height, that collimator-and-detector assembly can be adjusted and set to a different collimator height. Methods and systems of the invention can be adjusted accordingly for collecting data using collimator-and-detector assemblies that differ with respect to collimator height, collimator aperture, imaging geometry, or distance between an object subjected to the imaging and the collimator-and-detector assembly or between an x-ray source and the collimator-and-detector. Adjustments can be made to a single collimator-and-detector assembly or multiple collimator-and-detector assemblies can be used.

In this simulation, the form factor ($\theta^l e^{-c_2\theta}$) was adjusted for Rayleigh scattering such that the average Rayleigh scattering angle was 4.3°. In each run, TIM-OS traced a total of 2×10$^{10}$ x-ray photons.

FIGS. 4A-E provide several images showing the differences between images obtained by varying parameters of the system, including collimation aspect ratios and object-detector distance, as well as images produced by combining the various results. More particularly, FIGS. 4A and B present two images obtained with the varying collimation method: (A) an image obtained with a collimator of a high collimation aspect ratio 50 (IH), and a counterpart (B) with a low collimation aspect ratio 10 (IL).

By subtracting IH from IL, the Rayleigh scattering image of FIG. 4C. The varying collimation scheme correctly extracted the small angle scattering signals, and the signal intensities reflected the relative Rayleigh scattering percentages. Hence, Rayleigh scattering parameters based on the varying collimation scheme can be reconstructed similarly to reconstructing attenuation. Additionally, the small angle scattering information (e.g., data) can be extracted by capturing two images at different object-detector distances without changing the detector collimator physically. For example, by subtracting the longer distance image from the shorter distance image, we can digitally extract the small-angle scattering information. FIG. 4C is an image captured with a longer distance (17.5 cm) than FIG. 4B (2.5 cm) given the same collimation ratio (10). FIG. 4E shows the difference between these two images.

While Monte Carlo simulation provides the golden standard for small scattering imaging simulation, the single scattering method provides a faster way to estimate the small scattering signal. Thus, we used Eq. 6a to predict the single scattering image for the phantom in FIG. 3, assuming a low collimation ratio 10 and short detector-object distance 2.5 cm. Here the computation of $$\frac{1}{2\pi}\int_{\varphi_1}^{\varphi_2}d\varphi\int_{\theta_1}^{\theta_2}d\theta_p(\theta)$$

was completed in a Monte Carlo simulation in advance for 250 (=5 cm/0.02 cm) different depths and 5 different materials.

Figure 5B:
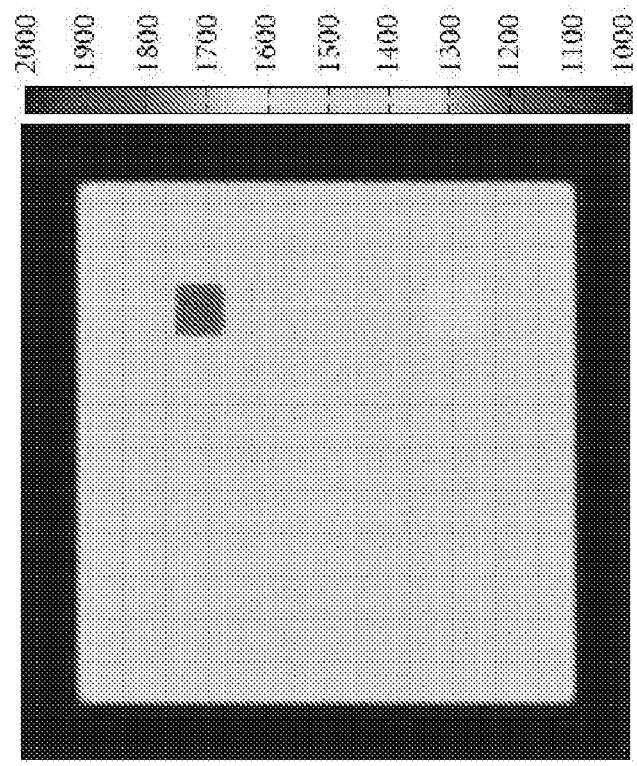
FIGS. 5A and B are images comparing results obtained from single scattering and small angle scattering scenarios.
Figure 5A:
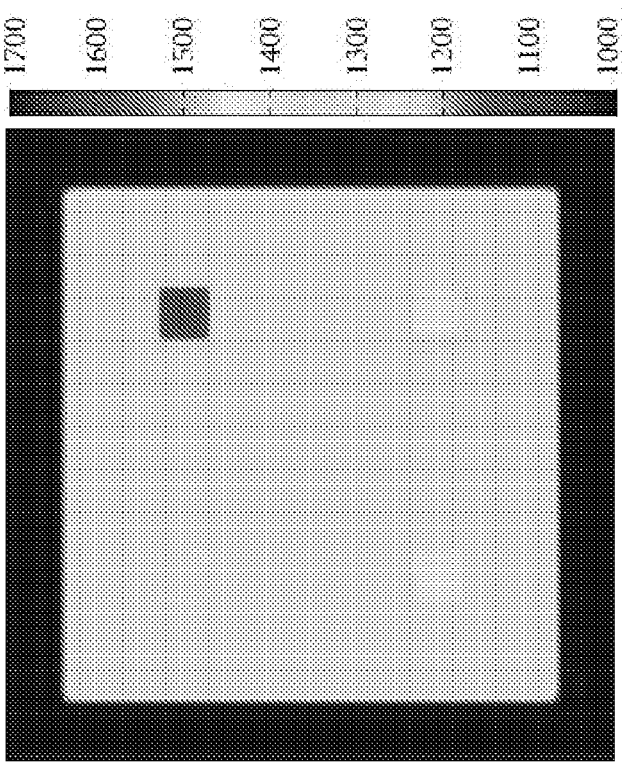

FIGS. 5A and B are images comparing results obtained from single scattering and small angle scattering scenarios. More particularly, FIG. 5A shows the numerical result according to the single scattering model Eq. 6a-6b and FIG. 5B shows the numerical result according to the Monte Carlo simulated small-angle scattering image. The Monte Carlo simulation took multiple scattering signals into account. Quantitatively, the Monte Carlo simulated small scattering image is about 10% higher than the single scattering image, which shows the validity or utility of the single scattering model in this type of application.

As described, embodiments of the invention provide methods and systems of a varying height collimation methodology for extraction of the dark-field signal for dark-field tomography. These methods and systems are advantageous in several aspects. Practically, the technology can be implemented by modifying existing collimation technology slightly. Technically, it allows volumetric scanning such as in circular and spiral cone-beam geometries. Potentially, it may be extended to probe other x-ray interactions with materials. The described approach has potential for a wide range of applications including medical imaging, security screening, industrial non-destructive testing, and so on.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

The invention claimed is:

1. A method for producing an x-ray image comprising:
providing at least one first dataset of primary x-ray signals as a majority of its data capable of being presented as a first image of an object subjected to x-ray imaging;
providing at least one second dataset comprising dark-field x-ray signals and primary x-ray signals as a majority of its data capable of being presented as a second image of the object;
combining the first dataset and the second dataset using a computer comprising a computer readable medium embedded with processing means for obtaining a target dataset having more dark-field (small-angle scattering) x-ray signals than the first or second dataset alone for producing a target image of the object which has higher contrast quality than the images based on the first or second dataset alone.

2. The method of claim 1 comprising providing the first and second datasets using collimator-and-detector assemblies or configurations that differ with respect to collimator height, collimator aperture, imaging geometry, or distance between an object subjected to the imaging and the collimator-and-detector assembly.

3. The method of claim 1, wherein the computer readable medium embedded with processing means is based on:
a) Radon transform data with respect to a small-angle scattering coefficient distribution derived from the principle of photon energy conservation:

$$\ln\left[1+\frac{T_s(r+R\theta)}{T_a(r+R\theta)}\right]=\int_0^R \mu_s(r+s\theta)\,ds \qquad (9.1)$$

where $$T_a(r+R\theta)=\frac{\Phi_a(r+R\theta)}{\Phi_0} \text{ and } T_s(r+R\theta)=\frac{\Phi_s(r+R\theta)}{\Phi_0}$$

are photon transmission and small-angle scattering transference relative to intensity of incident x-ray $\Phi_0$ respectively; $\Phi_a(r_0+R\theta)$ is intensity of transmission photons, and $\Phi_s(r_0+R\theta)$ is intensity of small-angle scattering photons, each of which is measured on a detector at distance R along projection angle $\theta$ from x-ray source position $r_0$; $\mu_s$ is the small-angle scattering coefficient; and r is a position after an object; or
b) another governing equation derived from the radiative transfer equation (RTE); or
c) another approximation to the radiative transfer equation (RTE).

4. The method of claim 3 further comprising a computer readable medium embedded with processing means for performing x-ray dark-field tomography (XDT) from the extracted dark-field x-ray data.

5. The method of claim 3, wherein the target image based on the extracted dark-field x-ray data is produced in a radiographic/2D mode.

6. The method of claim 3, wherein the target image based on the extracted dark-field x-ray data is produced in a tomographic or stereographical or tomosynthesis mode.

7. The method of claim 3 further comprising performing x-ray dark-field tomography (XDT) from the extracted dark-field data to characterize small-angle scattering properties in terms of one or more parameters, or to characterize small-angle scattering properties in terms of Rayleigh scattering coefficient, or to characterize Rayleigh scattering phase function.

8. A system for x-ray imaging comprising:
- a first collimator-and-detector assembly having a first operable configuration to provide at least one first dataset comprising primary x-ray signals as a majority of its data capable of being presented as a first image of an object subjected to x-ray imaging;
- a second collimator-and-detector assembly having a second operable configuration or wherein the first collimator-and-detector assembly is adjustable to a second configuration to provide at least one second dataset comprising primary and dark-field x-ray signals as a majority of its data capable of being presented as a second image of the object;
- a computer operably coupled with the collimator-and-detector assemblies comprising a computer readable medium embedded with processing means for combining the first dataset and the second dataset to extract the dark-field x-ray signals and produce a target image having higher contrast quality than the images based on the first or second dataset alone.

9. The system of claim 8, wherein at least two of the collimator-and-detector assemblies or configurations differ with respect to collimator height, collimator aperture, imaging geometry, or distance between an object subjected to the imaging and the collimator-and-detector assembly.

10. The system of claim 8, wherein the computer readable medium embedded with processing means is based on:
a) Radon transform data with respect to a small-angle scattering coefficient distribution derived from the principle of photon energy conservation:

$$\ln\left[1 + \frac{T_s(r + R\theta)}{T_a(r + R\theta)}\right] = \int_0^R \mu_s(r + s\theta) \, ds \qquad (9.1)$$

where $$T_a(r + R\theta) = \frac{\Phi_a(r + R\theta)}{\Phi_0} \text{ and } T_s(r + R\theta) = \frac{\Phi_s(r + R\theta)}{\Phi_0}$$

are photon transmission and small-angle scattering transference relative to intensity of incident x-ray $\Phi_0$, respectively; $\Phi_a(r_0+R\theta)$ is intensity of transmission photons, and $\Phi_s(r_0+R\theta)$ is intensity of small-angle scattering photons, each of which is measured on a detector located at distance R along projection angle e from x-ray source position $r_0$; $\mu_s$ is the small-angle scattering coefficient; and r is a position after an object; or
b) another governing equation derived from the radiative transfer equation (RTE); or
c) another approximation to the radiative transfer equation (RTE).

11. The system of claim 10 further comprising a computer readable medium embedded with processing means for performing x-ray dark-field tomography (XDT) from the extracted dark-field x-ray data.

12. A method of x-ray imaging comprising:
- collecting x-ray data with a collimator-and-detector assembly configured to provide at least one first dataset comprising primary x-ray signals as a majority of its data;
- adjusting the collimator-and-detector assembly to a second configuration for collecting at least one second dataset comprising primary and dark-field x-ray signals as a majority of its data or collecting the second dataset with a second collimator-and-detector assembly configuration;
- computing the first and second datasets with a computer operably coupled with the collimator-and-detector assembly and comprising a computer readable medium embedded with processing means for extracting the dark-field x-ray signals for producing a target image having a higher contrast quality than an image based on the first or second dataset alone.

13. The method of claim 12 further comprising collecting x-ray data with additional collimator-and-detector assemblies or additional collimator-and-detector adjustments and computing two or more of the datasets to extract the dark-field signals for producing an image.

14. The method of claim 12, wherein at least two of the collimator-and-detector assemblies or adjustments differ with respect to collimator height, collimator aperture, imaging geometry, or distance between an object subjected to the imaging and the collimator-and-detector assembly.

15. The method of claim 12, wherein the collecting data comprises detecting x-ray photons in a spectrally resolving fashion, or at least one collimator-and-detector assembly or adjustment is configured to detect Compton scattering photons in a spectrally resolving fashion.

16. The method according to claim 15 further comprising performing x-ray dark-field tomography (XDT) and Compton scattering imaging from the extracted spectral x-ray data.

17. The method of claim 12, wherein at least one collimator-and-detector assembly or adjustment is configured to allow fan-beam or cone-beam scanning along a general trajectory.

18. The method of claim 17, wherein the trajectory is circular or spiral loci.

19. The method of claim 12, wherein the computer readable medium embedded with processing means is based on:
a) Radon transform data with respect to a small-angle scattering coefficient distribution derived from the principle of photon energy conservation:

$$\ln\left[1 + \frac{T_s(r + R\theta)}{T_a(r + R\theta)}\right] = \int_0^R \mu_s(r + s\theta) \, ds \qquad (9.1)$$

where $$T_a(r + R\theta) = \frac{\Phi_a(r + R\theta)}{\Phi_0} \text{ and } T_s(r + R\theta) = \frac{\Phi_s(r + R\theta)}{\Phi_0}$$

are photon transmission and small-angle scattering transference relative to intensity of incident x-ray $\Phi_0$, respectively; $\Phi_a(r_0+R\theta)$ is intensity of transmission photons and $\Phi_s(r_0+R\theta)$ is intensity of small-angle scattering photons each of which is measured on a detector located at distance R along projection angle $\theta$ from x-ray source position $r_0$; $\mu_s$ is the small-angle scattering coefficient; and r is a position after an object; or
b) another governing equation derived from the radiative transfer equation (RTE); or
c) another approximation to the radiative transfer equation (RTE).

20. The method of claim 12, wherein the target image based on the extracted dark-field x-ray data is produced in a radiographic/2D mode.

21. The method of claim 12, wherein the target image based on the extracted dark-field x-ray data is produced in a tomographic or stereographical or tomosynthesis mode.

22. The method of claim 12 further comprising performing x-ray dark-field tomography (XDT) from the extracted dark-field data to characterize small-angle scattering properties in terms of one or more parameters, or to characterize small-angle scattering properties in terms of Rayleigh scattering coefficient, or to characterize Rayleigh scattering phase function.

* * * * *

UNITED STATES PATENT AND TRADEMARK OFFICE
CERTIFICATE OF CORRECTION

PATENT NO. : 8,121,249 B2  
APPLICATION NO. : 12/794160  
DATED : February 21, 2012  
INVENTOR(S) : Ge Wang and Wenxiang Cong Page 1 of 1

It is certified that error appears in the above-identified patent and that said Letters Patent is hereby corrected as shown below:

Specification

Column 1, Lines 14-17:

"This work was partially supported by the National Institutes of Health under Grants EB001685, EB006036, EB008476, CA135151 and CA127189. The U.S. Government has certain rights in the invention."

should be:

--This invention was made with government support under Grants EB001685, EB006036, EB008476, CA135151, and CA127189, awarded by National Institutes of Health. The government has certain rights in the invention.--

Signed and Sealed this  
Twentieth Day of October, 2015

Michelle K. Lee  
*Director of the United States Patent and Trademark Office*